US007709444B2

(12) United States Patent
Milton et al.

(10) Patent No.: US 7,709,444 B2
(45) Date of Patent: *May 4, 2010

(54) ECHINOCANDIN PHARMACEUTICAL FORMULATIONS CONTAINING MICELLE-FORMING SURFACTANTS

(75) Inventors: Nathaniel Milton, Indianapolis, IN (US); Kenneth Philip Moder, West Lafayette, IN (US); James Lawrence Sabatowski, Holland, MI (US); Stephanie Ann Sweetana, Bloomington, IN (US)

(73) Assignee: Pfizer Inc., New York, NY (US)

( * ) Notice: Subject to any disclaimer, the term of this patent is extended or adjusted under 35 U.S.C. 154(b) by 802 days.

This patent is subject to a terminal disclaimer.

(21) Appl. No.: 11/103,798

(22) Filed: Apr. 11, 2005

(65) Prior Publication Data

US 2005/0192213 A1 Sep. 1, 2005

Related U.S. Application Data

(63) Continuation of application No. 09/942,431, filed on Aug. 29, 2001, now Pat. No. 6,960,564, which is a continuation of application No. PCT/US00/05546, filed on Mar. 2, 2000.

(60) Provisional application No. 60/122,623, filed on Mar. 3, 1999.

(51) Int. Cl.
*A61K 38/12* (2006.01)

(52) U.S. Cl. .................. 514/11; 530/317; 424/400; 424/489

(58) Field of Classification Search .................. 514/11; 530/317; 424/400, 489
See application file for complete search history.

(56) References Cited

U.S. PATENT DOCUMENTS

| | | | |
|---|---|---|---|
| 3,978,210 A | 8/1976 | Mizuno et al. | |
| 4,293,482 A | 10/1981 | Abbott et al. | |
| 4,293,483 A | 10/1981 | Debono | |
| 4,293,489 A | 10/1981 | Debono | |
| 4,299,763 A | 11/1981 | Abbott et al. | |
| 4,304,716 A | 12/1981 | Abbott et al. | |
| 4,320,052 A | 3/1982 | Abbott et al. | |
| 4,348,384 A | 9/1982 | Horikoshi et al. | |
| 4,876,241 A | 10/1989 | Feldman et al. | |
| 4,927,831 A | 5/1990 | Malamas | |
| 5,141,674 A | 8/1992 | Leigh | |
| 5,166,135 A | 11/1992 | Schmatz | |
| 5,198,421 A | 3/1993 | Chen et al. | |
| 5,202,309 A | 4/1993 | Schwartz et al. | |
| 5,376,634 A | 12/1994 | Iwamoto et al. | |
| 5,541,160 A | 7/1996 | Balkovec et al. | |
| 5,573,936 A | 11/1996 | Kreuzman et al. | |
| 5,618,787 A | 4/1997 | Jamison et al. | |
| 5,629,289 A | 5/1997 | Rodriguez | |
| 5,629,290 A | 5/1997 | LaGrandeur et al. | |
| 5,646,111 A | 7/1997 | Borromeo et al. | |
| 5,652,213 A | 7/1997 | Jamison et al. | |
| 5,679,665 A | 10/1997 | Bergamini et al. | ......... 514/171 |
| 5,693,611 A | 12/1997 | Henle et al. | |
| 5,696,084 A | 12/1997 | Lartey et al. | |
| 5,741,775 A | 4/1998 | Balkovec et al. | |
| 5,786,325 A | 7/1998 | Borromeo et al. | |
| 5,932,543 A | 8/1999 | Burkhardt et al. | |
| 5,952,008 A | 9/1999 | Backstrom et al. | |
| 5,952,300 A | 9/1999 | Nerurkar et al. | |
| 5,965,525 A | 10/1999 | Burkhardt et al. | |
| 5,972,996 A | 10/1999 | Nielsen-Kahn et al. | |
| 5,985,309 A | 11/1999 | Edwards et al. | |
| 5,993,805 A | 11/1999 | Sutton et al. | |
| 5,994,338 A | 11/1999 | Bounine et al. | |
| 6,001,336 A | 12/1999 | Gordon | |
| 6,043,341 A | 3/2000 | Udodong et al. | |
| 6,136,783 A | 10/2000 | Nerurkar et al. | |
| 6,153,224 A | 11/2000 | Staniforth | |
| 6,258,821 B1 | 7/2001 | Stogniew et al. | |
| 6,267,958 B1 | 7/2001 | Andya et al. | |
| 6,284,277 B1 | 9/2001 | Bouloumie et al. | |
| 6,284,282 B1 | 9/2001 | Maa et al. | |
| 6,309,623 B1 | 10/2001 | Weers et al. | |
| 6,323,176 B1 | 11/2001 | Jamison et al. | |
| 6,331,521 B1 | 12/2001 | Hori et al. | |
| 6,384,013 B1 | 5/2002 | Burkhardt et al. | |

(Continued)

FOREIGN PATENT DOCUMENTS

CA 2043762 C 12/1991

(Continued)

OTHER PUBLICATIONS

McLean, Larry R. (Biochemistry (1991), 30(1), 31-7).*
Avis, K. E. (1990). "Parenteral Preparations" Chapter 84 In *Remington Pharmaceutical Sciences*. 18th edition, Mack Publishing Company p. 1545-1569.
Debono, M. et al. (1995). "Semisynthetic Chemical Modification of the Antifungal Lipopeptide Echinocandin B (ECB): Structure-Activity Studies of the Lipophilic and Geometric Parameters of Polyarylated Acyl Analogs of ECB," *J Med Chem*. 38(17):3271-3281.
Etter, M.C. and Baures, P.W. (1988) "Triphenylphosphine Oxide as a Crystallization Aid," *J. Am. Chem. Soc*. 110:639-640.
Groll, A. H. et al. (2001). "Pharmacokinetic and Pharmacodynamic Modeling of Anidulafungin (LY303366): Reappraisal of Its Efficacy in Neutropenic Animal Models of Opportunistic Mycoses Using Optimal Plasma Sampling," *Antimicrobial Agents and Chemotherapy* 45(10):2845-2855.

(Continued)

*Primary Examiner*—David Lukton
(74) *Attorney, Agent, or Firm*—Gregg C. Benson; Jason Tebbutt

(57) ABSTRACT

Pharmaceutical formulations are described comprising an echinocandin compound or echinocandin/carbohydrate complex and a pharmaceutically acceptable micelle-forming surfactant in a non-toxic aqueous solvent such that the solubilization of the echinocandin compound is optimized and the ability to freeze-dry the solution is maintained. Both the solution and freeze-dried formulations have increased stability. A bulking agent, tonicity agent buffer and/or a stabilizing agent may optionally be added to the formulations to further enhance the stability of the formulation.

29 Claims, No Drawings

U.S. PATENT DOCUMENTS

| | | | |
|---|---|---|---|
| 6,433,040 B1 | 8/2002 | Dellamary et al. |
| 6,451,349 B1 | 9/2002 | Robinson et al. |
| 6,475,523 B1 | 11/2002 | Staniforth |
| 6,506,726 B1 | 1/2003 | Dobbins et al. |
| 6,565,885 B1 | 5/2003 | Tarara et al. |
| 6,590,073 B2 | 7/2003 | Dalder et al. |
| 6,638,495 B2 | 10/2003 | Weers et al. |
| 6,653,281 B1 | 11/2003 | Borromeo et al. |
| 6,660,843 B1 | 12/2003 | Feige et al. |
| 6,670,324 B2 | 12/2003 | Jamison et al. |
| 6,689,390 B2 | 2/2004 | Bernstein et al. |
| 6,709,650 B1 | 3/2004 | Sutton et al. |
| 6,743,776 B2 | 6/2004 | Ohki et al. |
| 6,743,777 B1 | 6/2004 | Burkhardt et al. |
| 6,916,784 B2 | 7/2005 | Burkhardt et al. |
| 2002/0151474 A1 | 10/2002 | Schwier et al. |
| 2002/0160942 A1 | 10/2002 | Larew et al. |
| 2002/0161176 A1 | 10/2002 | Dalder et al. |
| 2003/0039667 A1 | 2/2003 | Jira et al. |
| 2003/0054981 A1 | 3/2003 | Milton et al. |
| 2003/0104048 A1 | 6/2003 | Patel et al. |
| 2003/0220236 A1 | 11/2003 | Burkhardt et al. |
| 2004/0223997 A1 | 11/2004 | Stogniew |

FOREIGN PATENT DOCUMENTS

| | | |
|---|---|---|
| EP | 0 031 221 A1 | 7/1981 |
| EP | 0 031 221 B1 | 7/1981 |
| EP | 0 032 009 A1 | 7/1981 |
| EP | 0 359 529 | 3/1990 |
| EP | 0 365 324 A1 | 4/1990 |
| EP | 0 365 324 B1 | 4/1990 |
| EP | 0 447 186 | 9/1991 |
| EP | 0 448 343 A2 | 9/1991 |
| EP | 0 448 343 A3 | 9/1991 |
| EP | 0 448 353 | 9/1991 |
| EP | 0 448 354 A2 | 9/1991 |
| EP | 0 448 354 A3 | 9/1991 |
| EP | 0 448 355 A2 | 9/1991 |
| EP | 0 448 355 A3 | 9/1991 |
| EP | 0 448 356 A2 | 9/1991 |
| EP | 0 448 356 A3 | 9/1991 |
| EP | 0 460 882 A1 | 12/1991 |
| EP | 0 462 531 | 12/1991 |
| EP | 0 486 011 A2 | 5/1992 |
| EP | 0 486 011 A3 | 5/1992 |
| EP | 0386951 | 5/1992 |
| EP | 0 503 960 A1 | 9/1992 |
| EP | 0 525 889 A1 | 2/1993 |
| EP | 0 561 639 A1 | 9/1993 |
| EP | 0 561 639 B1 | 9/1993 |
| EP | 0 589 074 A1 | 3/1994 |
| EP | 0 589 074 B1 | 3/1994 |
| EP | 0 744 405 A2 | 11/1996 |
| EP | 0 744 405 A3 | 11/1996 |
| EP | 0 744 405 B1 | 11/1996 |
| EP | 0 757 058 A1 | 2/1997 |
| EP | 0 757 058 B1 | 2/1997 |
| EP | 0 931 834 A2 | 7/1999 |
| EP | 0 931 834 A3 | 7/1999 |
| GB | 2241956 A | 9/1991 |
| GB | 2242194 A | 9/1991 |
| JP | 05-271097 A | 10/1993 |
| JP | 06-172205 A | 6/1994 |
| WO | WO-94/25048 | 11/1994 |
| WO | WO-95/27074 A1 | 10/1995 |
| WO | 9531971 | 11/1995 |
| WO | WO-96/31228 A1 | 10/1996 |
| WO | WO-96/37509 A1 | 11/1996 |
| WO | WO-96/37510 A1 | 11/1996 |
| WO | WO-96/37511 A1 | 11/1996 |
| WO | WO-96/37512 A1 | 11/1996 |
| WO | WO-97/05163 A1 | 2/1997 |
| WO | 9730695 | 8/1997 |
| WO | WO-97/27864 A1 | 8/1997 |
| WO | WO-97/30695 A1 | 8/1997 |
| WO | WO-99/06062 A1 | 2/1999 |
| WO | WO-99/43337 A1 | 9/1999 |
| WO | WO-00/11023 A2 | 3/2000 |
| WO | WO-00/11023 A3 | 3/2000 |
| WO | WO-00/12540 A1 | 3/2000 |
| WO | WO-00/34315 A2 | 6/2000 |
| WO | WO-00/34315 A3 | 6/2000 |
| WO | WO-00/35944 A1 | 6/2000 |
| WO | WO-00/35945 A1 | 6/2000 |
| WO | WO-00/51564 A1 | 9/2000 |
| WO | WO-00/51567 A1 | 9/2000 |
| WO | WO-00/52036 A1 | 9/2000 |
| WO | WO-00/52037 A1 | 9/2000 |
| WO | WO-03/105767 A2 | 12/2003 |
| WO | WO-03/105767 A3 | 12/2003 |

OTHER PUBLICATIONS

Ibrahim, F. S. et al., (1995) "The Effect of pH, sugars and calcium ion concentration on the thermal stability of whey proteins" *Egyptian J. Dairy Sci.* 23:177-178.

International Search Report for PCT Application No. PCT/US00/05494 filed Mar. 2, 2000, mailed Jun. 7, 2000, three pages.

International Search Report for PCT Application No. PCT/US00/05508 filed Mar. 2, 2000, mailed Aug. 21, 2000, two pages.

International Search Report for PCT Application No. PCT/US00/05546 filed Mar. 2, 2000, mailed Aug. 11, 2000, two pages.

International Search Report for PCT Application No. PCT/US00/05547 filed Mar. 2, 2000, mailed Jul. 19, 2000, three pages.

International Search Report for PCT Patent Application No. PCT/US03/18754 filed on Jun. 12, 2003, mailed on Dec. 9, 2003, 5 pages.

Keller-Juslen, C.M. et al. (1976). "Structure of the Cyclopeptide Antibiotic SL 7810 (=Echinocandin B)," *Tetrahedron Letters* 46:4147-4150.

Longer, M. A. and Robinson, J. R. (1990). "Transdermal Systems" in Chapter 91 In *Remington Pharmaceutical Sciences*. 18th edition, Mack Publishing Company. p. 1690-1693.

Nail, S. and Gatlin, L. A. (1993). "Freeze Drying Principles and Practice" Chapter 3 In *Pharmaceutical Dosage Forms*, 2nd edition. K. E. Avis ed. et al., Marcel Dekker, Inc. NY pp. 163-233.

Nema, S. et al. (1997). "Excipients and Their Use in Injectable Products," *PDA Journal of Pharm. Science and Tech.* 51(4):166-171.

Sclarra, J. J. and Cutie, A. J. (1990). "Aerosols" Chapter 92 In *Remington Pharmaceutical Sciences*. 18th edition, Mack Publishing Company. p. 1694-1712.

Turco, S. J. (1990). "Intravenous Admixtures," Chapter 85 In *Remington Pharmaceutical Sciences*. 18th edition, Mack Publishing Company. p. 1570-1580.

Turner, W.W. et al. (1996). "Recent Advances in the Medicinal Chemistry of Antifungal Agents," *Current Pharmaceutical Design* 2:209-224.

Sandoz-Patent-GMBH,—Derwent Publications Ltd.,582468/32. Abstract.

Patent Abstract of Japan, Publication No. 03-240727, Oct. 28, 1991, Toyo Jozo Co. Ltd.

Carpenter et al., Pharmaceutical Research, vol. 14, No. 8, pp. 969-975.

Hara Kazuyuki et al., English Abstract of JP3044333A, publication date Feb. 26, 1991.

Kimura Yukio et al., English Abstract of JP56068616A, publication date Jun. 9, 1981.

Prista. L., L. Nogusira & Cols., Tecnologia Farmacêutica, vol. II, 4$^{th}$ Edition, p. 931, 1995.

Sandoz-Patent-GmbH,—Derwent Publications Ltd., 582,468/32, Abstract (Jan. 1978).

Carpenter et al., Pharmaceutical Research, vol. 14, No. 8, pp. 969-975. (1997).

\* cited by examiner

ECHINOCANDIN PHARMACEUTICAL FORMULATIONS CONTAINING MICELLE-FORMING SURFACTANTS

CROSS-REFERENCE TO RELATED APPLICATIONS

This application is a continuation of U.S. patent application Ser. No. 09/942,431, filed on Aug. 29, 2001, now U.S. Pat. No. 6,960,564, which is a continuation of International Patent Application No. PCT/US00/05546, filed on Mar. 2, 2000, which claims priority to U.S. Provisional Patent Application Ser. No. 60/122,623, filed on Mar. 3, 1999, the contents of which are incorporated herein by reference in their entirety.

FIELD OF THE INVENTION

The present invention relates to pharmaceutical formulations containing an echinocandin compound, in particular, the incorporation of micelle-forming surfactants to enhance stability and water solubility.

BACKGROUND OF THE INVENTION

Parenteral (ip) formulations of pharmaceutical drugs may be administered to patients via intramuscular (im), intravenous (iv) or subcutaneous methodology. The formulation that is developed for a particular drug is dependent on a variety of issues. For example, it is well-known in the art that a formulation should be water-soluble and stable. If freeze-dried the formulation should be capable of forming a well-formed cake and readily reconstitutable (usually in less than one minute). Finally, the formulation should have an acceptable appearance and be prepared from generally accepted, safe excipients.

Stability is an important consideration when designing a formulation, especially for ip applications. For practical reasons, it must be possible to store the formulation for at least two years. Therefore, it is often desirable to freeze dry the formulation to achieve better shelf-life and storage at room temperature.

The instability and poor water solubility (<0.1 mg/ml) of the echinocandin compounds make them particularly difficult to formulate. Most of the formulations tested to date have a shelf life of less than one year. Generally, a shelf life of two or more years is a required. Consequently, a formulation containing an echinocandin compound may require freeze-drying to achieve the necessary stability.

The poor water solubility of the echinocandin compounds affords a further challenge in formulating an ip formulation containing echinocandin active materials. One method of formulating such compounds is by the addition of a surfactant which enhances the solubility of the drug. However, it is generally well-known in the art that the use of a surfactant above a certain concentration generally limits the ability to freeze dry the formulation. A typical freeze-dried formulation has a surfactant concentration less than 5% by weight. According to a market survey of freeze-dried pharmaceutical formulations containing surfactants, the surfactant concentration is usually less than 5% weight in the freeze dried product. See. Carpenter et al., Pharm. Res., 14 (8), 969-975, 1977 to 1997, *Physicians' Desk Reference.* 50$^{th}$ edition, Medical Economics. Co. N.J. (1996). It is generally believed that a formulation with higher concentrations of surfactant is not likely to form a freeze-dried product with desirable characteristics. Specifically, the presence of the surfactant causes the freeze-dried cake to "collapse" resulting in a residue at the bottom of the vial instead of a well-formed cake. The residue is generally less stable, difficult to reconstitute, and non-reproducible.

Because of the poor water solubility of the echinocandin compounds, generally 2-4% (weight by volume) of a surfactant is required to obtain an acceptable concentration of the echinocandin compound in solution. As discussed above, freeze-drying is hindered at this level of surfactant. Therefore, there is a need for a formulation that improves the solubility of echinocandin compounds in water yet allows freeze drying to obtain optimum stability.

SUMMARY OF THE INVENTION

Applicants have discovered a group of surfactants that solubilize echinocandin compounds at higher concentrations and surprisingly retain the ability to freeze dry the formulation. In one embodiment of the present invention, a parenteral pharmaceutical formulation is provided that comprises (i) an echinocandin compound (or a pharmaceutically acceptable salt thereof), (ii) a pharmaceutically acceptable, micelle-forming surfactant (e.g., polysorbates, lecithin, bile salts, polyoxyethylene castor oils and mixtures thereof), and (iii) a non-toxic, aqueous solvent. The pharmaceutical solution formulation may optionally contain one or more of a stabilizing agent, a tonicity agent and/or a buffer. The weight ratio of echinocandin to surfactant is from about 1:1.75 to about 1:25 (more preferably in a ratio of about 1:2 to about 1:3) and the echinocandin compound is present in an amount greater than or equal to 1 mg/ml. The surfactant is generally present in an amount greater than 1% weight per volume.

In one embodiment of the present invention, a freeze-dried pharmaceutical formulation is provided that comprises (i) an echinocandin compound (or a pharmaceutically acceptable salt thereof), (ii) a pharmaceutically acceptable, micelle-forming surfactant (e.g., polysorbates, lecithin, bile salts, polyoxyethylene castor oils, and mixtures thereof), and (iii) a bulking agent. The micelle-forming surfactant is present in an amount greater than 5% by weight in the freeze dried product and the ratio of echinocandin to surfactant is from about 1:1.75 to about 1:25 (preferably in a ratio of about 1:2 to about 1:3). The pharmaceutical freeze-dried formulation may optionally contain one or more of a stabilizing agent and/or a buffer. A parenteral pharmaceutical formulation prepared from the freeze-dried formulation is also provided.

In yet another embodiment of the present invention, a process is provided for preparing a parenteral formulation, which comprises mixing an echinocandin compound (or echinocandin/carbohydrate complex) and a pharmaceutically acceptable, micelle-forming surfactant in an aqueous solvent.

In another embodiment of the present invention, a process is provided for making a freeze-dried formulation comprising in the following order the steps of: (i) dissolving into an aqueous solvent an echinocandin compound (or echinocandin/carbohydrate complex) in the presence of a pharmaceutically acceptable, micelle-forming surfactant, wherein the surfactant is present in an amount greater than 1% weight by volume; (ii) sterile filtering the solution; and (iii) freeze-drying the solution. Generally, a bulking agent is added before freeze-drying the solution. Optionally, one may add one or more buffers, stabilizing agents, tonicity agents, or combinations thereof before step (iii).

An alternative preparation for a freeze-dried formulation is also provided which comprises (i) buffering a non-toxic aqueous solvent to a pH between 4.0 and 5.0 to form a buffered solution; (ii) adding to the buffered solution a pharmaceutically acceptable, micelle-forming surfactant; (iii) cooling the solution from step (ii) to a temperature between 5° and 15° C. (preferably between 7° and 10° C.) to form a cooled solution; (iv) adding a slurry comprising an echinocandin compound or echinocandin/carbohydrate complex and a second non-toxic aqueous solvent to the cooled solution; (v) sterile filtering said solution from step (iv); and (vi) freeze-drying said solution from step (v). One or more bulking agents, stabilizing agents and/or tonicity agents may optionally be added prior to step (v).

In another embodiment of the present invention, a parenteral pharmaceutical product is provided which is prepared by dissolving into an aqueous solvent an echinocandin compound (or echinocandin/carbohydrate complex) in the presence of a pharmaceutically acceptable, micelle-forming surfactant to form a solution, wherein the surfactant is present in an amount greater than 1% weight per volume; (ii) sterile filtering the solution; and (iii) freeze-drying the solution in a vial, wherein the weight ratio of echinocandin to surfactant is from about 1:1.75 to about 1:25. When ready for use, a non-toxic, aqueous solvent is added to the vial.

In yet another embodiment of the present invention, a method is provided for treating an antifungal infection in a mammal in need thereof, which comprises administering to the mammal the parenteral formulation described above or a parenteral formulation prepared by adding a pharmaceutically acceptable aqueous solvent to one of the freeze-dried formulations described above.

Amounts and percentages are described herein as weight units unless otherwise stated.

The term "echinocandin" refers to a compound having the following general structure:

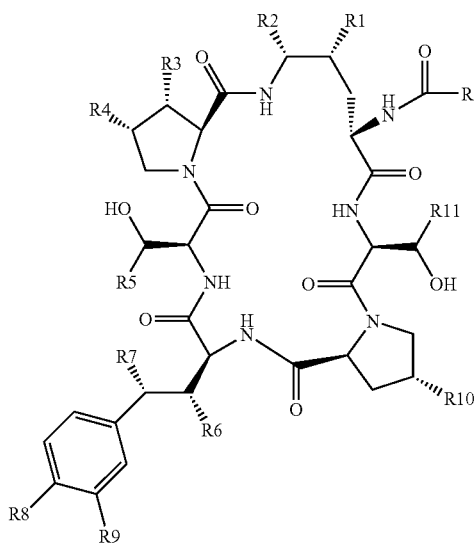

where: R is an alkyl group, an alkenyl group, an alkynyl group, an aryl group, heteroaryl group, or combinations thereof; $R_1$, $R_2$, $R_3$, $R_6$, $R_7$, and $R_{10}$ are independently hydroxy or hydrogen; $R_4$ is hydrogen, methyl or —$CH_2C(O)NH_2$; $R_5$ and $R_{11}$ are independently methyl or hydrogen; $R_4$ is —OH, —$OPO_3H_2$, —$OPO_3HCH_3$, —$OPO_2HCH_3$, or —$OSO_3H$; and $R_9$ is —H, —OH, or —$OSO_3H$.

The term "alkyl" refers to a hydrocarbon radical of the general formula $C_nH_{2n+1}$ containing from 1 to 30 carbon atoms unless otherwise indicated. The alkane radical may be straight, branched, cyclic, or multi-cyclic. The alkane radical may be substituted or unsubstituted. Similarly, the alkyl portion of an alkoxy group or alkanoate have the same definition as above.

The term "alkenyl" refers to an acyclic hydrocarbon containing at least one carbon-carbon double bond. The alkene radical may be straight, branched, cyclic, or multi-cyclic. The alkene radical may be substituted or unsubstituted.

The term "alkynyl" refers to an acyclic hydrocarbon containing at least one carbon carbon triple bond. The alkyne radical may be straight, or branched. The alkyne radical may be substituted or unsubstituted.

The term "aryl" refers to aromatic moieties having single (e.g., phenyl) or fused ring systems (e.g., naphthalene, anthracene, phenanthrene, etc.). The aryl groups may be substituted or unsubstituted. Substituted aryl groups include a chain of aromatic moieties (e.g., biphenyl, terphenyl, phenylnaphthalyl, etc.).

The term "heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

Within the field of organic chemistry and particularly within the field of organic biochemistry, it is widely understood that significant substitution of compounds is tolerated or even useful. In the present invention, for example, the term alkyl group allows for substituents which is a classic alkyl, such as methyl, ethyl, isopropyl, isobutyl, tertiary butyl, hexyl, isooctyl, dodecyl, stearyl, etc. The term group specifically envisions and allows for substitutions on alkyls which are common in the art, such as hydroxy, halogen, alkoxy, carbonyl, keto, ester, carbamato, etc., as well as including the unsubstituted alkyl moiety. However, it is generally understood by those skilled in the art that the substituents should be selected so as to not adversely affect the pharmacological characteristics of the compound or adversely interfere with the use of the medicament. Suitable substituents for any of the groups defined above include alkyl, alkenyl, alkynyl, aryl, halo, hydroxy, alkoxy, aryloxy, mercapto, alkylthio, arylthio, mono- and di-alkyl amino, quaternary ammonium salts, aminoalkoxy, hydroxyalkylamino, aminoalkylthio, carbamyl, carbonyl, carboxy, glycolyl, glycyl, hydrazino, guanyl, and combinations thereof.

"Echinocandin/carbohydrate complex" refers to a crystalline complex formed between an echinocandin compound and a carbohydrate when the echinocandin is recrystallized from a solvent in the presence of the carbohydrate. A more detailed description of the echinocandin/carbohydrate complexes may be found in Larew, et al., filed on Mar. 3, 1999, and assigned publication number WO0052037, entitled "Echinocandin/Carbohydrate Complexes."

"Carbohydrate" refers to an aldehydic or ketonic derivative of polyhydric alcohols represented by the formulas $C_n(H_2O)_n$ (e.g., glucose, $C_6(H_2O)_6$; sucrose, $C_{12}(H_2O)_{11}$). Carbohydrates include compounds with relatively small molecules, such as the simple sugars (e.g., monosaccharides, disaccharides, etc.), as well as macromolecular (polymeric) substances such as starch, glycogen, and cellulose polysaccharides. Sugars are carbohydrates (saccharides) having the general composition $(CH_2O)_n$ and simple derivatives thereof. Although the simple monomeric sugars (glycoses) are described as polyhydroxy aldehydes or ketones, e.g., $HOCH_2$—$(CHOH)_4$—CHO for aldohexoses (e.g., glucose) or $HOCH_2$—$(CHOH)_3$—CO—$CH_2OH$ for 2-ketoses (e.g., fructose), the structures are commonly written as five (furanose) or six (pyranose) membered ring cyclic ethers, e.g.

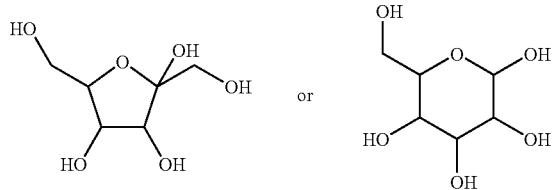

The term "micelle-forming surfactant" refers to an amphiphilic material that spontaneously and reversibly forms a water soluble aggregate. For a more detailed description of micelle formation and a listing of micelle-forming surfactants see Attwood et al. *Surfactant Systems, Their Chemistry, Pharmacy and Biology*, Chapman and Hall (1983). Block copolymers of propylene oxide and ethylene oxide do not perform well in the formulations of the present invention; therefore, these block copolymers are not considered within the meaning of micelle-forming surfactants.

The term "pharmaceutically acceptable" when used herein as an adjective, means substantially non-toxic and substantially non-deleterious to the recipient.

DETAILED DESCRIPTION

The cyclic peptides used in the present invention may be produced by culturing various microorganisms. Suitable natural product starting materials belonging to the echinocandin cyclic peptide family include Echinocandin B, Echinocandin C, Echinocandin D, Aculeacin Aγ, Mulundocandin, Sporiofungin A, Pneumocandin $A_0$, WF11899A, and Pneumocandin $B_0$. In general, the cyclic peptides may be characterized as a cyclic hexapeptide nucleus with an acylated amino group on one of the amino acids. The amino group on the naturally-occurring cyclic peptide is typically acylated with a fatty acid group forming a side chain off the nucleus. Examples of naturally-occurring acyl groups include linoleoyl (Echinocandin B, C and D), palmitoyl (Aculeacin Aγ and WF11899A), stearoyl, 12-methylmyristoyl (Mulundocandin), 10,12-dimethylmyristoyl (Sporiofungin A and Pneumocandin $A_0$) and the like.

Semi-synthetic derivatives may be prepared by removing the fatty acid side chain from the cyclic peptide nucleus to produce a free amino group (i.e. no pendant acyl group —C(O)R). The free amine is then reacylated with a suitable acyl group. For example, the echinocandin B nucleus has been re-acylated with certain non-naturally occurring side chain moieties to provide a number of antifungal agents. See, i.e., U.S. Pat. No. 4,293,489. Those skilled in the art will appreciate that the N-acyl side chain encompasses a variety of side chain moieties known in the art. Suitable side chain moieties include substituted and unsubstituted alkyl groups, alkenyl groups, alkynyl groups, aryl groups, heteroaryl groups and combinations thereof. Preferably, the side chain contains both a linearly rigid section and a flexible alkyl section to maximize antifungal potency. Representative examples of preferred acyl side chains include R groups having the following structures:

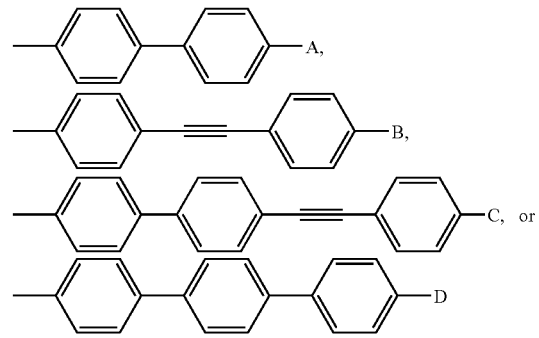

where A, B, C and D are independently hydrogen, $C_1$-$C_{12}$ alkyl $C_2$-$C_{12}$ alkynyl, $C_1$-$C_{12}$ alkoxy, $C_1$-$C_{12}$ alkylthio, halo, or —O—$(CH_2)_m$—[O—$(CH_2)_n]_p$—O—($C_1$-$C_{12}$ alkyl), or —O—$(CH_2)_q$—X-E; m is 2, 3 or 4; n is 2, 3 or 4; p is 0 or 1; q is 2, 3 or 4; X is pyrrolidino, piperidino or piperazino; and E is hydrogen, $C_1$-$C_{12}$ alkyl, $C_3$-$C_{12}$ cycloalkyl, benzyl or $C_3$-$C_{12}$ cycloalkylmethyl.

As noted above, the cyclic peptides described herein may be prepared by fermentation of known microorganisms as described in the art. The subsequent deacylation is typically carried out enzymatically using a deacylase enzyme by known materials and procedures described in the art.

For example, U.S. Pat. No. 4,293,482 describes the deacylation and preparation of the cyclic peptide of formula I where $R_4$, $R_5$, and $R_{11}$ are methyl, $R_9$ is hydrogen, and $R_1$, $R_2$, $R_3$, $R_6$, $R_7$, $R_8$ and $R_{10}$ are each hydroxy. U.S. Pat. No. 4,299,763 describes the deacylation and preparation of the cyclic peptide of formula I where $R_4$, $R_5$, and $R_{11}$ are methyl, $R_2$ is hydroxy, $R_7$ and $R_9$ are hydrogen and $R_1$, $R_3$, $R_6$, $R_8$ and $R_{10}$ are each hydroxy. U.S. Pat. No. 3,978,210 describes the preparation of aculeacin. U.S. Pat. No. 4,304,716 describes the deacylation and preparation of the cyclic peptide of formula I where $R_5$ is —$CH_2C(O)NH_2$; $R_{11}$ is methyl; $R_4$ and $R_9$ are hydrogen; $R_1$, $R_2$, $R_3$, $R_6$, $R_7$, $R_8$ and $R_{10}$ are each hydroxy and the acyl group with substituent R is myristoyl.

Cyclic peptides where $R_2$ and $R_7$ are each hydrogen may be prepared by subjecting the corresponding compound (where $R_2$ and $R_7$ are each hydroxy; the ornithine alpha-amino group may be a free amino group or acylated) to a strong acid and a reducing agent at a temperature of between −5° C. and 70° C., in a suitable solvent. Suitable strong acids include trichloroacetic acid, trifluoroacetic acid or boron trifluoride etherate. A preferred strong acid is trifluoroacetic acid. Suitable reducing agents include sodium cyanoborohydride or triethylsilane. A preferred reducing agent is triethylsilane. Suitable solvents include methylene chloride, chloroform or acetic acid, preferably methylene chloride. The strong acid is present in an amount from about 2 to 60 mol per mol of substrate, and the reducing agent is present in an amount from about 2 to 60 mol per mol of substrate. The acid reduction process selectively removes the aminal ($R_2$) and benzylic ($R_7$) hydroxy groups.

Acylation of the α-amino group on the ornithine unit may be accomplished in a variety of ways well known to those skilled in the art. For example, the amino group may be acylated by reaction with an appropriately substituted acyl halide, preferably in the presence of an acid scavenger such as a tertiary amine (e.g., triethylamine). The reaction is typically carried out at a temperature between about −20° C. to 25° C. Suitable reaction solvents include polar aprotic solvents, such as dioxane or dimethylformamide. Solvent choice is not critical so long as the solvent employed is inert to the ongoing reaction and the reactants are sufficiently solubilized to effect the desired reaction.

The amino group may also be acylated by reaction with an appropriately substituted carboxylic acid, in the presence of a coupling agent. Suitable coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazole-1-yloxy-tripyrrolidinophosphonium hexafluorophosphate (PyBOP) and the like.

Alternately, the amino group may be acylated with an activated ester of a carboxylic acid such as p-nitrophenyl, 2,4,5-trichlorophenyl, hydroxybenzotriazole hydrate (HOBT.$H_2O$), pentafluorophenol, and N-hydroxysuccinimide carboxylate esters. Preferred acylating moieties are the 2,4,5-trichlorophenyl and HOBT carboxylate esters. The reaction is typically ran 1 to 65 hours at a temperature from about 0° C. to 30° C. in an aprotic solvent. The reaction is generally complete after about 24 to 48 hours when carried out at a temperature between about 15° C. to 30° C. Suitable solvents include tetrahydrofuran and dimethylformamide or mixtures thereof. The amino group is generally present in equimolar proportions relative to the activated ester or with a slight excess of the amino group.

The R—COOH precursor acids are prepared by hydrolyzing a nitrile of the formula R—CN or an ester of the formula R—COO($C_1$-$C_4$ alkyl). The nitrile and ester intermediates may be prepared using procedures known in the art. For example, the nitrile and ester intermediates where R is an alkoxy aryl moiety may be prepared using Procedure A or Procedure B.

Procedure A One equivalent of an alkyl bromide, iodide, or p-toluenesulfonate is added to a mixture containing one equivalent of a base, such as potassium t-butoxide or potassium carbonate ($K_2CO_3$), and one equivalent of an hydroxy aryl compound in 200-300 ml of acetonitrile ($CH_3CN$). The reaction mixture is refluxed for 6 h and then concentrated in vacuo to provide a residue which is dissolved in a $Et_2O$/2N NaOH mixture. The resulting layers are separated and the organic layer is dried over magnesium sulfate ($MgSO_4$), filtered and dried to provide the alkoxy aryl product.

Procedure B Diethylazodicarboxylate (1 equiv.) is added dropwise to a mixture containing an hydroxy aryl compound (1 equiv.), an alkyl alcohol (1 equiv.) and triphenylphosphine (1 equiv.) in 200-300 ml of THF. After 17 h, the solvent is removed in vacuo to provide a residue which is dissolved in $Et_2O$. The resulting mixture is washed with a 2N NaOH solution, dried over $MgSO_4$, filtered and concentrated to provide a product which is then crystallized from a $Et_2O$/pentane mixture or, if the product contains a tertiary amine, the hydrochloride salt is formed and crystallized from a methanol (MeOH)/EtOAc mixture. The nitrile and ester intermediates where R is an alkynyl aryl moiety may be prepared using Procedure C.

Procedure C A mixture containing $Et_2O$ (2 equiv.), palladium dichloride (0.05 equiv.), triphenylphosphine (0.1 equiv.), cuprous iodide (0.025 equiv.) and an alkyne (1 equiv.) is added to one equivalent of an aryl bromide, iodide, or trifluoromethanesulfonate in $CH_3CN$ (600 ml/0.1 mol of aryl reactant), under nitrogen ($N_2$). The resulting mixture is refluxed for 17 h and then the solvent is removed in vacuo to provide a residue which is slurried in 300 ml of $Et_2O$ and then filtered. The filtrate is washed with a 1N HCl solution, dried over $MgSO_4$, filtered and then dried to provide the product. The ester intermediates where R is a terphenyl moiety may be prepared using Procedure D.

Procedure D

1. Formation of Boronic Acid Reactant

Butyl lithium (1.2 equivalents) is added to one equivalent of a cold (−78° C.) aryl halide in THF. After 15 minutes, triisopropyl borate (2 equiv.) is added. After 10 minutes, the reaction mixture is warmed to room temperature and quenched by the addition of water ($H_2O$), followed by the addition of 1N HCl. The resulting layers are separated and the organic layer is concentrated in vacuo to provide a solid which is collected by filtration and washed with hexane.

2. Formation of Terphenyl Ester

Tetrakis(triphenylphosphine)palladium (0.03 equiv.) is added to a mixture containing an aryl boronic acid (1 equiv.), $K_2CO_3$ (1.5 equiv.) and methyl 4-iodobenzoate (1 equiv.) (or trichlorophenyl ester of iodobenzoate) in $N_2$-purged toluene. The reaction mixture is refluxed for 7 h and then decanted to remove the $K_2CO_3$ and dried in vacuo to provide a residue. This residue is triturated in $CH_3CN$ and filtered to provide the product. The aryl nitriles and esters described above may be converted to the corresponding carboxylic acids by hydrolysis using Procedure E or Procedure F.

Procedure E An aryl nitrile is dissolved in ethanol (EtOH) and an excess of 50% NaOH solution and refluxed for 2 h. Water is added to the reaction mixture until a solid precipitates. This solid is collected by filtration, added to a dioxane/6N HCl mixture and the resulting mixture is refluxed for 17 h. When the reaction is substantially complete, the carboxylic acid product is crystallized by the addition of $H_2O$ and then collected by filtration and dried in vacuo.

Procedure F An excess of 2N NaOH is added to an aryl ester in MeOH, and the resulting solution is refluxed for 5 h and then acidified by the addition of excess HCl. Water is added to the reaction mixture until a solid (carboxylic acid) precipitates. The carboxylic acid is collected by filtration and dried in vacuo. The carboxylic acids may be converted to the corresponding 2,4,5-trichlorophenyl esters using Procedure G, below. The activated esters are then used to acylate the amino nucleus.

Procedure G A mixture containing an aryl carboxylic acid (1 equiv.), 2,4,5-trichlorophenol (1 equiv.) and DCC (1 equiv.) in $CH_2Cl_2$ is stirred for 17 h and then filtered. The filtrate is concentrated to provide a residue which is dissolved in $Et_2O$, filtered, and then pentane is added until crystallization begins. The crystals are collected by filtration and dried in vacuo. Alternatively, the carboxylic acid may be activated by conversion to the corresponding hydroxybenzotriazole ester using Procedure H.

Procedure H An aryl carboxylic acid (1 equiv.) and a slight excess of N-mesylate substituted hydroxybenzotriazole (1.2 equiv.) were reacted in the presence of a slight excess of a base such as triethylamine ($Et_3N$) (1.3 equiv.) in DMF, under $N_2$. When the reaction was complete, the mixture was diluted with toluene and washed with $H_2O$. The organic portion was diluted with $H_2O$ and then filtered using t-butyl methyl ether (MTBE) for transferring the material. The resultant solid was washed with MTBE and then dried in vacuo.

The echinocandin compound may be isolated and used per se or in the form of its pharmaceutically acceptable salt or hydrate, or as a echinocandin/carbohydrate complex. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogen-phosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like.

"Echinocandin/carbohydrate complex" refers to a crystalline complex formed between an echinocandin compound and a carbohydrate (or sugar) when the echinocandin is recrystallized from a solvent in the presence of the carbohydrate. A more detailed description of the echinocandin/carbohydrate complexes may be found in Larew, et al., filed on Mar. 3, 1999, and assigned publication number WO0052037, entitled "Echinocandin/Carbohydrate Complexes" and incorporated herein by reference. The complexes are formed using standard crystallization procedures such as those typically performed for purifying compounds by recrystallization. The echinocandin material and carbohydrate are dissolved at an elevated temperature (approximately 45 to 60° C., preferably less than 55° C.) in a solvent. The solution is then slowly cooled until the crystallization begins. A seed crystal (such as a previously crystallized complex or an insoluble sugar) may be added to initiate crystallization. Suitable solvents include any solvent, or mixture of solvents, inert to the ongoing reaction that sufficiently solubilizes the reactants to afford a medium within which to effect the desired complexation between the carbohydrate and the echinocandin compound, such as protic or ketone solvents including methanol, ethanol, benzyl alcohol, as well as mixtures of benzyl alcohol with solvents such as methanol, ethanol, n-propanol, isopropanol, n-butanol, 2-butanol, t-butanol, 2-pentanol, 2-methyl-1-propanol, MEK, acetone, ethyl acetate, toluene, acetonitrile, fluorobenzene, methylene chloride, nitromethane, or cyclic ketones such as cyclopentanone and cyclohexanone. Preferred solvents include methanol, ethanol, benzyl alcohol, and mixtures of benzyl alcohol with methyl ethyl ketone, ethyl acetate, and acetonitrile.

Suitable carbohydrates include adonitol, arabinose, arabitol, ascorbic acid, chitin, D-cellubiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose and hydrates thereof. Suitable carbohydrates also include the D and L enantiomers, as well as the alpha and beta anomers of the compounds listed above. Preferred carbohydrates are the simple sugars (e.g., mono- and di-saccharides).

The echinocandin compound can be present in a formulation of the present invention prior to freeze drying at concentrations greater than or equal to 1 mg/ml. Generally, the echinocandin compound is present in a range from about 1 mg/ml to about 50 mg/ml, preferably at a concentration in the range from about 1 mg/ml to about 40 mg/ml, more preferably from about 1 mg/ml to about 30 mg/ml and most preferably from about 8 mg/ml to about 12 mg/ml.

The formulations of the present invention contain a micelle-forming surfactant that is a pharmaceutically acceptable amphiphilic excipient having hydrophobic and hydrophilic units or groups which are capable of solubilizing a non-water soluble drug in water. HLB values of 10-18 are generally most favorable for solubilization of the echinocandin compounds. The surfactant is present in the formulation at a weight ratio of echinocandin to surfactant from about 1:1.75 to about 1:25, more preferably in a ratio of about 1:2 to about 1:3. The upper limit of surfactant added to the formulation may be limited by its toxicity in application of the pharmaceutical medicament; therefore, the upper limit may vary depending upon the particular surfactant selected. Suitable surfactants include polysorbates (e.g., polysorbate 80, polysorbate 40, polysorbate 20), polyoxyethylene castor oil derivatives (e.g., Cremophors™ (polyoxyl 35 castor oil, polyoxyl 40 hydrogenated castor oil, and polyoxyl 60 hydrogenated castor oil) available from BASF)), polyoxyethylene stearates (e.g., Solutol™ HS 15 (macrogol-660-hydroxystearate, available from BASF), sorbitan trioleate, bile salts (e.g., cholic acids, deoxycholic acids and salts thereof (e.g., sodium deoxycholate or sodium taurodeoxycholate)), lecithin, and the like. Preferred surfactants include polysorbate 80, polysorbate 40, polysorbate 20, and polyoxyethylene hydroxystearates having reduced histamine effects (e.g., Solutol™ HS 15). Surfactants that do not solubilize well include certain poloxamers which are block copolymers of propylene oxide and ethylene oxide.

"Polysorbate" refers to materials having the following general structure:

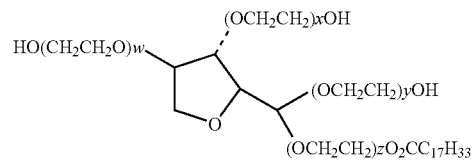

where x+y+w+z is equal to an integer between 5 and 20.

The commercial product Tween™ 20, 40 and 80 (available from ICI Americas Inc., Wilmington, Del.) are represented by the above structure when x+y+w+z=20.

"Lecithin" refers to materials having the following general structure:

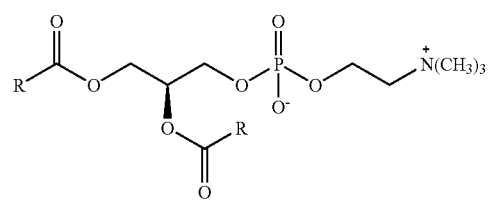

R is typically the residue from stearic acid, palmitic acid or oleic acid.

"Bile salts" refer to materials having the following general structure:

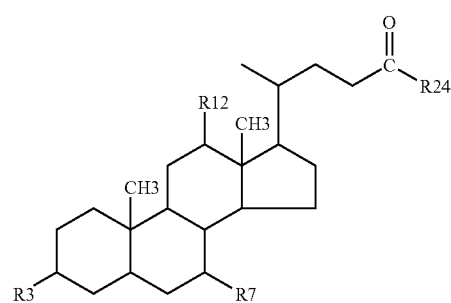

where $R_3$, $R_7$, and $R_{12}$ are —OH, —H or —SO$_3^-$ groups and $R_{24}$ is —OH or an alkali salt of —CO$_2^-$, —C(O)NH(CH$_2$)$_n$SO$_3^-$, or —C(O)NH(CH$_2$)$_n$CO$_2^-$ and n is equal to an integer between 1 and 4.

A typical solution formulation includes an echinocandin compound and a micelle-forming surfactant. Applicants have observed that the incorporation of the micelle-forming surfactant not only optimizes the solubilization of the echinocandin compound but also enhances the stability of the solution. The formulation may optionally include one or more of a buffer, a stabilizing agent, and/or a tonicity agent. If the formulation is in the form of a solution then a solvent is also present. Solvents are generally selected based on solvents recognized as safe (GRAS) to be administered parenterally to a mammal. In general, safe solvents are non-toxic aqueous solvents such as, water and other non-toxic solvents that are soluble or miscible in water. Suitable solvents include water, ethanol, propylene glycol, polyethylene glycols (e.g., PEG400, PEG300), etc. and mixtures thereof. A preferred solvent is water.

A typical freeze-dried formulation includes an echinocandin compound, a pharmaceutically acceptable micelle-forming surfactant, a bulking agent and/or a stabilizing agent. The formulation may optionally include one or more buffering agents. Applicants have observed that the addition of the micelle-forming surfactant not only optimizes the reconstitution of the freeze-dried formulation in a non-toxic aqueous solvent but also provides enhanced stability to the freeze-dried materials.

Both solution and freeze-dried formulations may optionally contain a stabilizing agent. A stabilizing agent is generally present at a concentration in the range from about 0.5% to about 40% (wgt./vol.), more preferably at a concentration in the range from about 1% to about 6%. The term "stabilizing agent" refers to a pharmaceutically acceptable excipient that enhances the chemical or physical stability of the active ingredient in the formulation. Suitable stabilizing agents include polyols (e.g., polyethylene and propylene glycols, and carbohydrates such as sucrose, trehalose, fructose, lactose and mannitol), amino acids and surfactants such as polysorbates and bile salts. Preferred stabilizing agents for freeze dried formulation include mannitol, sucrose, trehalose, fructose, lactose and combinations thereof. In solution most preferred stabilizing agents are the bile salts, polyethylene glycols and propylene glycol.

Both solution and freeze-dried formulations may also optionally contain a buffer. The buffer is present at a concentration in the range from about 0.03% to about 5.0% (wgt./vol.), more preferably at a concentration in the range from about 0.1% to about 1.0%. The term "buffer" refers to a pharmaceutically acceptable excipient that maintains the pH of the solution within a particular range specific to the buffering system. A suitable pH range is from pH 3.0-7.0. Preferably the pH range is from 4.0-5.5, more preferably 4.0-5.0. Suitable buffers include acetates, citrates, phosphates, tartrates, lactates, succinates, amino acids and the like. Preferred buffers for the solution formulation include acetate, citrate, tartrates, phosphate salts and combinations thereof. For the freeze dried formulation, the preferred buffer is tartaric acid.

Solution formulations may optionally contain one or more tonicity agents. The tonicity agent is generally present at a concentration in the range from about 1 to about 100 mg/ml, more preferably in the range from about 9 to about 50 mg/ml. The term "tonicity agent" refers to a pharmaceutically acceptable excipient that makes the solution compatible with blood. Tonicity agents are desirable in injectable formulations. Suitable tonicity agents include glycerin, lactose, mannitol, dextrose, sodium chloride, sodium sulfate, sorbitol and the like. Preferred tonicity agents include mannitol, sorbitol, lactose and sodium chloride and combinations thereof.

When freeze-dried, the formulations may optionally contain a bulking agent. The bulking agent is present in a formulation at a concentration in the range from about 2% to about 10% (wgt./vol.), more preferably at a concentration in the range from about 3% to about 6%. The term "bulking agent" refers to a pharmaceutically acceptable excipient that adds bulk to a formulation which results in a well-formed cake upon freeze drying. Suitable bulking agents include mannitol, glycine, lactose, sucrose, trehalose, dextran, hydroxyethyl starch, ficoll and gelatin. Preferred bulking agents include mannitol, sucrose, trehalose, lactose and combinations thereof.

The formulations may be prepared using conventional dissolution and mixing procedures. For example, the bulk drug substance (e.g., echinocandin compound or echinocandin/carbohydrate complex) is dissolved in a non-toxic aqueous solvent in the presence of a pharmaceutically acceptable micelle-forming surfactant and optionally one or more bulking agents, buffers, stabilizing agents and/or tonicity agents. The resulting solution is then sterile filtered and preferably freeze-dried to provide the desired formulation. Prior to freeze drying, the surfactant is generally present in an amount greater than 1% weight per volume of solution.

Alternatively, the pharmaceutical solution may be prepared by forming an aqueous buffer solution buffered to a pH from about 3.0 to 7.0 (preferably from 4.0 to 5.5, more preferably from about 4.0 to 5.0). The buffer used may be any of the buffers described earlier. The micelle-forming surfactant is then added to the buffered solution and the solution cooled to about 5° to 15° C. (preferably about 7° to 10° C.). A slurry of the echinocandin compound or echinocandin/carbohydrate complex in a non-toxic aqueous solvent (which may or may not be the same as the solvent used in the buffer solution) is added to the cooled solution containing the surfactant. One or more bulking agents, stabilizing agents and/or tonicity agents may be added to the solution prior to freeze-drying. The resultant solution is then diluted with addition solvent, filtered and freeze-dried to provide the desired formulation.

A suitable method for freeze-drying is described in Nail et al. Freeze Drying Principles and Practice, in Pharmaceutical Dosage Forms, $2^{nd}$ Ed. Marcel Dekker, Inc. NY, pp. 163-233 (1993). The formulation is preferably freeze-dried in a vial which can then be stored until needed. A non-toxic, aqueous solvent is added to the vial to dissolve the freeze-dried material thus forming a solution that can be used in a parenteral therapeutic application. Those skilled in the art will appreciate that the aqueous solvent includes other common solutions used in such applications (e.g., saline solutions, dextrose solutions, etc.).

In general, freeze-dried formulations contain a bulking agent and non freeze-dried formulations contain one or more tonicity agents. In application, the formulations are typically diluted or reconstituted (if freeze-dried) and further diluted if necessary, prior to administration. An example of reconstitution instructions for the freeze-dried product are to add ten ml of water for injection (WFI) to the vial and gently agitate to dissolve. Typical reconstitution times are less than one minute. The resulting solution is then further diluted in an infusion solution such as dextrose 5% in water (D5W), prior to administration.

The active ingredient is typically formulated into pharmaceutical dosage forms to provide an easily controllable dosage of the drug and to give the patient an elegant and easily handleable product. Formulations may comprise from 0.1% to 60% by weight of active ingredient, more generally from about 10% to about 30% by weight.

As used herein, the term "unit dose" or "unit dosage" refers to physically discrete units that contain a predetermined quantity of active ingredient calculated to produce a desired therapeutic effect. When a unit dose is administered parenterally, it is typically provided in the form of measured units in ampoules (or vials).

The dosage to be administered may vary depending upon the physical characteristics of the patient, the severity of the patient's symptoms, and the means used to administer the drug. The specific dose for a given patient is usually set by the judgment of the attending physician.

Suitable carriers, diluents and excipients are known in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. The formulations may also include wetting agents, lubricating agents, emulsifiers, suspending agents, preservatives, sweeteners, perfuming agents, flavoring agents and combinations thereof.

A pharmaceutical composition may be administered using a variety of methods. Suitable methods include injection. The particular treatment method used will depend upon the type of infection being addressed.

Echinocandin and semi-synthetic echinocandin compounds have been shown to exhibit antifungal and antiparasitic activity such as growth inhibition of various infectious fungi including *Candida* spp. (i.e., *C. Albicans, C. Parapsilosis, C. Krusei, C. Glabrata, C. Tropicalis,* or *C. Lusitaniaw*); *Torulopus* spp. (i.e., *T. Glabrata*); *Aspergillus* spp. (i.e., *A. Fumigatus*); *Histoplasma* spp. (i.e., *H. Capsulatum*); *Cryptococcus* spp. (i.e., *C. Neoformans*); *Blastomyces* spp. (i.e., *B. Dermatitidis*); *Fusarium* spp.; *Trichophyton* spp., *Pseudallescheria boydii, Coccidioides immits, Sporothrix schenckii,* etc.

Compounds of this type also inhibit the growth of certain organisms primarily responsible for opportunistic infections in immunosuppressed individuals, such as growth inhibition of *Pneumocystis carinii* (the causative organism of *pneumocystis* pneumonia (PCP) in AIDS and other immunocompromised patients. Other protozoans that are inhibited by echinocandin-type compounds include *Plasmodium* spp., *Leishmania* spp., *Trypanosoma* spp., *Cryptosporidium* spp., *Isospora* spp., *Cyclospora* spp., *Trichomnas* spp., *Microsporidiosis* spp., etc.

Consequently, the formulations of the present invention are useful in combating either systemic fungal infections or fungal skin infections. Accordingly, the processes and formulations of the present invention may be used in the manufacture of a medicament for the therapeutic applications described herein. For example, fungal activity (preferably, *Candida albicans* or *Aspergillus fumigatis* activity) or parasitic activity may be inhibited by contacting a pharmaceutical formulation prepared by the present invention with a fungus or parasite, respectively. The term "contacting" includes a union or junction, or apparent touching or mutual tangency of a compound of the invention with a parasite or fungus. The term does not imply any further limitations to the process, such as by mechanism of inhibition. The methods are defined to encompass the inhibition of parasitic and fungal activity by the action of the compounds and their inherent antiparasitic and antifungal properties.

A method for treating a fungal infection which comprises administering an effective amount of a pharmaceutical formulation of the present invention to a host in need of such treatment is also provided. A preferred method includes treating a *Candida albicans* or *Aspergillus fumigatis* infection. The term "effective amount" refers to an amount of active compound which is capable of inhibiting fungal activity. The dose administered will vary depending on such factors as the nature and severity of the infection, the age and general health of the host and the tolerance of the host to the antifungal agent. The particular dose regimen likewise may vary according to these factors. The medicament may be given in a single daily dose or in multiple doses during the day. The regimen may last from about 2-3 days to about 2-3 weeks or longer. A typical daily dose (administered in single or divided doses) contains a dosage level between about 0.01 mg/kg to 100 mg/kg of body weight of an active compound. Preferred daily doses are generally between about 0.1 mg/kg to 60 mg/kg and more preferably between about 2.5 mg/kg to 40 mg/kg.

The following examples are provided to illustrate but not limit the invention. All references cited herein are hereby incorporated herein by reference.

EXAMPLES

The echinocandin compound used to exemplify the formulations of the present invention was prepared as described in the following preparations. Specifically, the following sequence describes the preparation of anti-fungal compound 6(a) having the following structure:

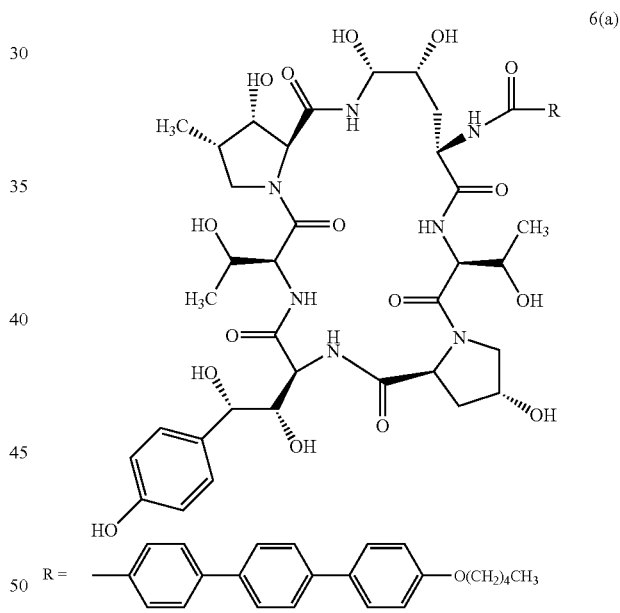

It will be understood by those skilled in the art that the following serves as an illustrative example and that other semi-synthetic echinocandin compounds useful as anti-fungal agents may be synthesized using similar procedures or procedures described in references cited earlier in the specification. Materials used ill the following preparations are available from Aldrich Chemicals (Milwaukee, Wis.) unless designated otherwise.

COMPOUND PREPARATIONS

Preparation of 4-Bromo-4'-pentyloxybiphenyl 1(a)

Anhydrous $K_2CO_3$ (416 g, 3 mol) was added to a mixture of 4-bromo-4'-hydroxybiphenyl (300 g, 1.2 mol), 1-iodopentane (234 ml, 1.79 mol) and 2-butanone (600 ml). The reaction mixture was refluxed for 44 h until TLC (85:15 hexanes/EtOAc) showed complete consumption of the bromo alcohol. The mixture was cooled to about 30° C., diluted with CH$_2$Cl$_2$ (600 ml) and then filtered. The filtrate was washed twice with H$_2$O and twice with a saturated aqueous NaCl solution, dried over anhydrous Na$_2$SO$_4$, filtered and then dried at reduced pressure to provide a solid. This solid was isolated by filtration, washed repeatedly with a total of 2 L of ice-cold heptane to remove all traces of iodopentane and then dried overnight under high vacuum. Yield: 340 g (88%) of a white powder.

Alternative Preparation of
4-bromo-4'-pentyloxybiphenyl 1(a)

4-Bromo-4'-hydroxybiphenyl (12.5 g, 50.2 mmol) was added to a solution of NaOH (2.28 g, 97% pure, 55.2 mmol) in deionized H$_2$O (150 ml), followed by the addition of 1-iodopentane (11.9 g, 60.2 mmol) and tetrabutylammonium bromide (0.82 g, 2.51 mmol). The mixture was stirred at 90° C. for 3.75 h until the solids went into solution. Then, as the reaction proceeded, the desired product began to precipitate. The mixture was slowly cooled and then filtered to provide a solid which was washed with deionized water until the pH of the filtrate was neutral and then dried for 16 h in a vacuum oven at 30° C.

Yield: 15.41 g (96%) of 5a. R$_f$ 0.5 (97:3 hexanes/EtOAc). $^1$H NMR: δ 0.93 (t, 3H, J=6.9 Hz); 1.41 (m, 4H) 1.79 (m, 2H); 3.97 (t, 2H, J=6.6 Hz); 6.98 (m, 2H); 7.23 (m, 6H). $^{13}$C NMR: δ 14.03; 22.43; 28.22; 28.98; 68.12; 114.91; 120.71; 127.93; 128.27; 131.77; 132.24; 139.82; 159.03. MS(FAB$^+$): m/z 320. IR(CHCl$_3$): 2960, 2936, 2874, 1608, 1518, 1485, 1475 cm$^{-1}$. Analysis for C$_{17}$H$_{19}$BrO: Calcd: C, 63.96; H, 6.00; Br, 25.0; Found: C, 64.10; H, 5.97; Br, 25.28.

Preparation of 4-Boronic acid-
4'-pentyloxybiphenyl 2(a)

To a cold (−20° C.) mixture of Compound 1(a) (100 g, 0.31 mol) in t-butylmethylether (MTBE) (1 L), was slowly added n-butyl lithium (150 ml of a 2.5M hexanes solution, 0.37 mol) dropwise under N$_2$, while maintaining the internal temperature between −19° and —18° C. The resultant mixture was stirred for 3.5 h between −17° and −16° C. which resulted in a light yellow-green solution. This solution was cooled to −78° C. and diluted with 100 ml of anhydrous THF which resulted in a white precipitate. Then, a cold (−78° C.) solution of triisopropylborate (145 ml, 0.62 mol) in MTBE (200 ml), under nitrogen was added dropwise over 1.5 h while maintaining the reaction temperature between −78° and −74° C. The resultant reaction mixture was stirred for 1.5 h at −78° C., then allowed to warm to −50° C. over 1 h at which time the cooling bath was removed and the mixture was stirred overnight (16-21 h) which resulted in a white precipitate. The mixture was shaken vigorously with 2M HCl (1000 ml) for 5 minutes and then the resulting layers were separated and the organic layer was dried at reduced pressure to provide a residue. This residue was diluted with MTBE (100 ml), followed by heptane (800 ml) to provide a white powder which isolated by suction filtration and washed 3 times with heptane (300 ml).

Yield: 88 g (98%). R$_f$ 0.45 (95:5 CH$_2$Cl$_2$/MeOH). $^1$H NMR: δ 0.92 (m, 3H); 1.41 (m, 4H); 1.80 (m, 2H); 4.00 (m, 2H); 6.99 (m, 2H); 7.45-7.63 (m, 3H); 7.67 (m, 2H); 8.24 (d, 1H, J=8.3 Hz). $^{13}$C NMR: 14.01; 22.26; 28.03; 28.77; 39.61; 39.89; 40.17; 40.45; 67.82; 114.77; 125.32; 127.83; 132.93; 134.84; 141.88; 158.71. MS(FD$^-$): m/z 284. IR(CHCl$_3$): 2959, 2952, 2874, 1606, 1526, 1500 cm$^{-1}$.

Preparation of Compound 3(a)

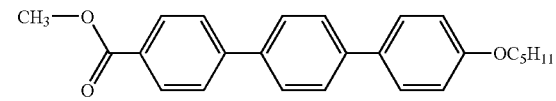

3(a)

A solution of toluene (174 ml) and propanol (20 ml) was degassed 3 times by applying vacuum to the solution for 20-30 seconds followed by purging with N$_2$. A 2M solution of Na$_2$CO$_3$ was also degassed. The toluene/propanol solution (97 ml) was added to a mixture of methyl 4-iodobenzoate (14.12 g, 53.9 mmol) and Compound 2(a) (15.0 g, 52.8 mmol), followed by a degassed 2M aqueous Na$_2$CO$_3$ solution (29 ml, 58.0 mmol). The resultant mixture was degassed 2 times for 20-30 seconds each under a positive pressure of N$_2$, followed by the addition of palladium (II) acetate (0.24 g, 1.1 mmol) and triphenylphosphine (0.84 g, 3.2 mmol) and then degassed 2 more times. The reaction mixture was then refluxed under N$_2$ for 5 h resulting in a light-yellow mixture. This mixture was cooled to 23° C. resulting in the formation of a precipitate which was collected by filtration, washed successively with toluene (123 ml), 2:1 MTBE/EtOAc (143 ml), deionized water (123 ml) and 2:1 MTBE/EtOAc (42 ml) and then dried for 16 h in a vacuum oven at 35° C. Yield: 18.7 g (94%). R$_f$ 0.48 (benzene). $^1$H NMR: δ 0.93 (t, 3H, J=6.80 Hz); 1.42 (m, 4H); 1.81 (m, 2H); 3.95 (s, 3H); 4.00 (t, 2H, J=6.48 Hz); 6.97 (d, 2H, J=8.52 Hz); 7.55 (d, 2H, J=8.52 Hz); 7.66 (m, 6H); 8.10 (d, 2H, J=8.20 Hz). MS(FD$^-$): m/z 374. IR(KBr): 2938, 1723 cm$^{-1}$. Analysis for C$_{25}$H$_{26}$O$_3$: Calcd: C, 80.18; H, 7.00; Found: C, 79.91; H, 6.94.

Preparation of Compound 4(a)

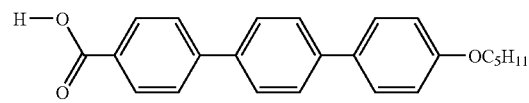

4(a)

A mixture of Compound 3(a) (80 g, 0.21 mol), 5M KOH (160 ml) and cetyltrimethylammonium bromide (4.8 g, 0.013 mol) in xylene (800 ml) was refluxed for 3 h and then cooled to 10° C. and filtered to provide a white solid. This solid was washed 3 times with H$_2$O (500 ml each) to remove the catalyst and most of the base. The resultant material was treated with DME (500 ml). The pH of the solution was adjusted to pH by the addition of 6M HCl (100 ml). The resultant mixture was refluxed for 30 minutes while periodically checking the pH to assure that it remained acidic, then cooled and filtered. The resulting solid was washed successively with MTBE (400 ml) and water (4×400 ml) until the washings were neutral to litmus. Yield: 76 g (98% yield). $^1$H NMR δ 0.89 (t, 3H, J=6.82 Hz), 1.38 (m, 4H), 1.73 (m, 2H), 3.96 (t, 2H, J=6.3 Hz), 6.95 (d, 2H, J=8.56 Hz), 7.57 (d, 2H, J=8.54 Hz), 7.64-7.74 (m, 6H), 8.00 (d, 2H, J=8.21 Hz), 8.09 (s, 1H). MS(FD$^+$) m/z 360. IR(KBr): 2958, 2937, 2872, 1688 cm$^{-1}$. Analysis for C$_{24}$H$_{24}$O$_3$: Calcd: C, 79.97; H, 6.71; Found: C, 80.50; H, 6.77.

Preparation of HOBT Ester of Compound 4(a)

A. Formation of HOBT Mesylate

To a cold (0° C.) mixture of hydroxybenzotriazole hydrate (200 g, 1.48 mol) in anhydrous $CH_2Cl_2$ (1.5 L), was slowly added anhydrous $Et_3N$ (268 ml, 1.92 mol) while maintaining a temperature of 0-10° C., followed by the addition of methanesulfonyl chloride (126 ml, 1.63 mol) while maintaining a temperature of 0-5° C. The resultant mixture was stirred for 3 h at 0° C. and washed successively with cold water (2×1.2 L) and brine (1.2 L). The combined organic extracts were concentrated at reduced pressure to provide a solid. This solid was recrystallized from $CH_2Cl_2$ (100 ml) and heptane (1 L). The crystals were collected by suction filtration and washed repeatedly with a total of 1. L of heptane and then dried overnight under high vacuum (0.5 mm Hg). Yield: 245 g (78%) $R_f$ 0.55 (1:1 hexanes/$CH_2Cl_2$). $^1$H NMR: δ 3.58 (s, 3H), 7.46 (t, 1H, J=7.60 Hz), 7.60 (d, 1H, J=8.28 Hz), 7.65 (d, 1H, J=8.56 Hz). 7.68 (d, 1H, J=8.20 Hz), 8.05 (d, 1H, J=8.41 Hz).

B. Formation of HOBT Ester

A mixture of Compound 4(a) (50 g, 0.14 mol) and the material described above in part A (36 g, 0.17 mol) in DMF (650 ml) was treated dropwise with $Et_3N$ (25 ml, 0.18 mol), under $N_2$. The resultant mixture was stirred for 4 h at room temperature until all the acid was consumed, as determined by TLC (95:5 $CH_2Cl_2$/MeOH). When all the acid was consumed, an aliquot of the reaction mixture (~3 pipes drops) gave a clear homogeneous solution when diluted with 3 ml of 1:1 $CH_2Cl_2$/THF. The reaction mixture was then diluted with toluene (500 ml), washed with water (500 ml). The organic layer (containing solid product) was diluted with water (500 ml) and filtered using MTBE for transferring. The solid was rinsed with MTBE (2×400 ml) and dried under vacuum to provide green-white flakes of material. NOTE: This material could be dissolved in THF and filtered to remove any remaining metal contamination. Yield: 61 g (92%). $R_f$ 0.68 (1:1 $CH_2Cl_2$/hexanes). $^1$H NMR: δ 0.93 (t, 3H, J=7.0 Hz), 1.42 (m, 4H), 1.81 (m, 2H), 4.00 (t, 2H, J=6.53 Hz), 6.99 (d, 2H, J=8.6 Hz), 7.42-7.59 (m, 5H), 7.71 (dd, 4H, J=13.91 Hz, 8.40 Hz), 7.86 (d, 2H, J=8.30 Hz), 8.11 (d, 1H, J=8.31 Hz), 8.35 (d, 2H, J=8.33 Hz). $^{13}$C NMR: δ 14.03, 22.44, 28.18, 28.94, 40.10, 40.37, 68.11, 108.45, 110.11, 114.95, 118.71, 120.48, 123.04, 124.94, 124.99, 127.00, 127.23, 127.51, 127.73, 128.06, 128.82, 128.86, 131.35, 132.30, 137.15, 141.43, 143.54, 147.85, 159.15, 162.73. MS(FD$^+$): m/z 477. IR(CHCl$_3$): 2960, 2936, 2874, 1783, 1606 cm$^{-1}$. Analysis for $C_{30}H_{27}N_3O_3$: Calcd: C, 75.45; H, 5.70; N, 8.80; Found: C, 75.69; H, 5.58; N, 8.92.

Preparation of Anti-Fungal Compound 6(a)

Deionized water was used throughout the procedure. A mixture of Compound 5(a) (11 g, 23 mmol) and the nucleus of Compound 6(a) (where R is hydrogen—92% pure by HPLC, 19.25 g, 22.2 mmol) in anhydrous DMF (275 ml) was stirred, under $N_2$ for 4 h (until HPLC showed complete consumption of the cyclic peptide starting material). The mixture was filtered through a bed of celite and the filtrate was concentrated under reduced pressure at 35° C. to provide a paste that could be stirred. This paste was poured into MTBE (500 ml) which resulted in the precipitation of a fine powder which was collected by vacuum filtration and dried to provide 27 g of crude material. This material was crushed to a powder with a mortar and pestle, slurried for 5 minutes in toluene (200 ml), suction filtered (slow filtered), rinsed with MTBE (100 ml) and then dried in vacuo to provide a yellow solid. Yield: 23 g (95% pure by HPLC, retention time=7.79 min).

Alternatively, the conversion may be carried out using an excess of the cyclic nucleus (1.1 equiv.). When the reaction is substantially complete, as indicated by HPLC, the crude material (10 g of a powder) is added portion-wise to a vigorously stirred mixture of 9:1 acetone/water (60 ml). Celite (2.5 g, pre-washed with a 9:1 acetone/water mixture) is added to the resultant suspension. After stirring for 2 minutes, the mixture is filtered through a bed of celite (prewashed with 9:1 acetone/water) and the cake is rinsed twice with 9:1 acetone/water (10 ml). The filtrate is poured into a beaker of deionized water (200 ml) while gently swirling the mixture which resulted in the formation of a precipitate. This precipitate is collected by suction filtration, rinsed with $H_2O$ (4×25 ml), and then dried in vacuo at room temperature. Yield: 6.81 g (97% pure by HPLC).

The product was further purified using preparatory HPLC chromatography. $R_f$ 0.29 (80:20 CHCl$_3$/MeOH). MS(FAB$^+$): m/z for $C_{58}H_{74}N_7O_7$, Calcd: 1140.5141; Found: 1140.5103. IR(KBr): 3365, 2934, 1632, 1518 cm$^{-1}$.

Pharmaceutical Formulations

The following Examples illustrate the formulations of the invention and methods for their preparation. The Examples are not intended to limit the scope of the invention in any respect and should not be so construed.

The following formulations were prepared by Method A. Method B or Method C. The quantity of Compound 6(a) was determined by calculating the theoretical potency needed for the experiments and dividing that value by the "as-is" HPLC potency of the compound.

Method A After adjusting the pH of 50 ml of a 0.1 M citrate buffer stock solution to pH 4, 2.5 g of polysorbate 80 was added and the resultant mixture was mixed until dissolved, followed by the addition of 1 g of the compound of Preparation 6(a) (potency). The resultant mixture was mixed until dissolved, followed by the addition of 3 g of mannitol (bulking agent) and 2 g of trehalose (stabilizing agent). The resultant mixture was again mixed until dissolved. The resultant solution was diluted with water to 100 ml in a volumetric flask. A 3 ml sample of this solution was transferred to a vial and then freeze-dried in a lyophilizer.

Method B The pH of a solution of 0.3005 g of acetic acid in 50 ml of water was adjusted to pH 4.0 using a 1N sodium hydroxide solution. While mixing, 2.5 g of polysorbate 80 and 5.0 g of mannitol (bulking agent) were added and the resultant mixture was mixed until dissolved, followed by the addition of 1 g of Compound 6(a) (potency). The resultant mixture was again mixed until dissolved. The resultant solution was diluted with water to 100 ml in a volumetric flask, filtered and then filled into vials. The vials may be freeze-dried in a lyophilizer or stored at 5° C.

Method C The pH of a solution of 0.113 g of tartaric in 50 ml of water was adjusted to pH 4.3 using a 10% sodium hydroxide solution. While mixing, 2.5 g of polysorbate 80 was added and mixed until dissolved. The temperature of the solution was reduced to 5-15° C. followed by the addition of 1 g of Compound 6(a) (potency) as a slurry in water. The resultant mixture was again mixed until dissolved followed by the addition of 1.0 g of fructose (stabilizing agent) and 5.0 g of mannitol (bulking agent). The resultant mixture was again mixed until dissolved. The resultant solution was diluted with water to 100 ml in a volumetric flask, filtered and then filled into vials. The vials may be freeze-dried in a lyophilizer or stored at 5° C.

The following Formulation Examples 1-27 were prepared substantially in accordance with Methods A and B, described above. The symbol "-" means that the designated ingredient was omitted from the formulation. In Table 1 and subsequent tables, all weights are in (grams); concentrations (⊕) are in mg/ml; CA stands for citric acid; Y stands for yes; N stands for no; Man stands for mannitol; Tre stands for trehalose; Col. stands for Collapse Cake; C stands for citrate; BA stands for bulking agent; B stands for buffer; PEG is polyethylene glycol; PPG is polypropylene glycol; SA stands for stabilizing agent; Ace is acetate; Poly 80 is polysorbate 80; Com is compound; Suc is sucrose; His is histidine; Sur is surfactant; Lac is lactose; Fru is fructose; TA is tartaric acid; and AA is acetic acid.

TABLE 1

| Ex No | Comp 6(a) | Poly 80 | BA | B | SA | Col. |
|---|---|---|---|---|---|---|
| 1 | 1 | 2.5 | Man(3) | CA(0.960) | Tre(2) | Y |
| 2 | 1 | 2.5 | Man(3) | CA(0.960) | Suc(2) | Y |
| 3 | 1 | 2.5 | — | CA(0.960) | Suc(5) | Partial |
| 4 | 1 | 2.5 | — | CA(0.960) | Tre(5) | Partial |
| 5 | 1 | 2.5 | — | — | Tre(5) | Partial |
| 6 | 1 | 2.5 | — | — | Suc(5) | Partial |
| 7 | 1 | 2.5 | — | — | Lac(5) | Partial |
| 8 | 1 | 2.5 | Man(5) | — | — | N |
| 9 | 1 | 2.5 | Man(5) | — | Suc(1) | N |
| 10 | 1 | 2.5 | Man(5) | — | Lac(1) | N |
| 11 | 1 | 2.5 | Man(5) | CA(0.096) | Lac(1) | N |
| 12 | 1 | 2.5 | Man(5) | TA(0.113) | Lac(1) | N |
| 13 | 1 | 2.5 | Man(5) | TA(0.113) | Fru(1) | N |
| 14 | 1 | 2.5 | Man(5) | — | PEG 8000(1) | N |
| 15 | 1 | 2.5 | Man(5) | — | PEG 6000(2) | N |
| 16 | 1 | 2.5 | Man(5) | — | His(0.5) Suc(0.5) | N |
| 17 | 1 | 2.5 | Man(5) | CA(0.960) | Suc(0.5) | N |
| 18 | 1 | 2.5 | Man(5) | CA(0.960) | Suc(1) | N |
| 19 | 1 | 2.5 | Man(5) | AA(0.3) | — | N |
| 20 | 0.1 | 2.5 | Man(5) | AA(0.3) | — | N |
| 21 | 0.1 | 2.5 | Man(5) | AA(0.6) | — | N |
| 22 | 0.1 | 2.5 | Man(5) | AA(0.06) | — | N |
| 23 | 0.1 | 2.5 | Man(5) | CA(1.92) | — | N |
| 24 | 0.1 | 2.5 | Man(5) | CA(0.19) | — | N |
| 25 | 0.1 | 2.5 | Man(5) | CA(0.960) | — | N |
| 26 | 0.5 | 1.25 | Man(5) | — | Lac(1) | N |
| 27 | 0.8 | 2.0 | Man(5) | — | Lac(1) | N | determined by visual observation

Solubility Studies

Solubility studies were performed at room temperature by transferring 5 ml of test solution (surfactant in water optionally containing a bulking agent, a buffer or a stabilizing agent) and 50 mg of Com 6(a) into a glass test tube. The test tubes were agitated overnight and examined for excess solid. Test tubes containing excess solid were removed for analysis. An additional 50 mg Compound 6(a) was added to test tubes which did not contain excess solids and the resultant mixture was agitated again. This process was repeated until excess solid was observed in the test tube. All samples were allowed to stand 1 h, supernatant was removed, filtered and analyzed by reverse phase HPLC to determine the potency of Com 6(a) per Ml of solution.

TABLE 2

| Sur(s) | [Sur] | Comp6(a) Potency |
|---|---|---|
| None | — | <0.1 |
| Poly 80 | 5 | 1 |
| Poly 80 | 10 | 4.4 |
| Poly 80 | 15 | 7.2 |
| Poly 80 | 25 | 13.2 |
| Poly 20/ Poly 80 | 5 5 | 4.8 |
| Poly 20/ Poly 80 | 5 10 | 8.0 |
| ethoxylated castor oil (cremophor™ EL) | 25 | 11.0 |
| Poly 20/ pluronic™ F68 | 5 10 | 1.13 |
| Poly 80/sodium taurodeoxycholate | 20 20 | 43.12 |

The stability of solution and freeze-dried formulations was evaluated by monitoring a sample of the formulation for the percent increase in related substances by reverse phase HPLC at initial, 2 weeks and 4 weeks of storage at 40° C.

TABLE 3

| 6(a) Potency (mg/ml) | Sur | B | Ton.Agent | Co-solvent (wgt %/vol) | Percent Related Substances | | |
|---|---|---|---|---|---|---|---|
| | | | | | 0 wks | 2 wks | 4 wks |
| 1 | Poly 80(25) | Cit(1.9) | Man(50) | — | 3.42 | 8.91 | 18.04 |
| 1 | Poly 80(25) | Cit(9.6) | Man(50) | — | 3.36 | 9.25 | 17.29 |
| 1 | Poly 80(25) | Cit(19.2) | Man(50) | — | 3.47 | 9.70 | 18.02 |
| 1 | Poly 80(25) | Ace(0.6) | Man(50) | — | 3.15 | 11.37 | 19.44 |
| 1 | Poly 80(25) | Ace(3) | Man(50) | — | 3.33 | 12.20 | 18.29 |
| 1 | Poly 80(25) | Ace(6) | Man(50) | — | 3.27 | 11.07 | 19.59 |
| 10 | Poly 80(25) | Ace(3) | — | — | 2.51 | 9.46 | 14.39 |
| 10 | Poly 80(20) Poly 20(5) | Ace(6) | — | — | 2.65 | 11.06 | 15.44 |
| 10 | Poly 80(15) Poly 20(10) | Ace(6) | — | — | 2.70 | 10.55 | 15.34 |
| 10 | Poly 80(5) Poly 20(20) | Ace(6) | — | — | 2.67 | 9.77 | 15.57 |
| 10 | Poly 80(25) | Ace(6) | — | 20% PEG400 | 2.83 | 9.69 | 14.35 |
| 10 | Poly 80(25) | Ace(6) | — | 40% PEG400 | 2.57 | 10.38 | 13.36 |
| 10 | Poly 80(25) | Ace(6) | — | 20% PPG | 2.71 | 10.58 | 13.40 |
| 10 | Poly 80(25) | Ace(6) | — | 40% PPG | 2.72 | 9.84 | 12.65 |
| 10 | Poly 80(25) | — | — | — | 3.62 | 18.71 | 27.91 |
| 10 | Poly 80(25) | — | Man(50) | — | 3.68 | 16.65 | 23.68 |
| 10 | Poly 80(25) | — | — | 40% PEG 400 | 3.73 | 15.26 | 23.99 |
| 10 | Poly 80(25) | — | — | 1% PEG 3350 | 3.68 | 21.56 | — |

TABLE 4

| 6(a) | | | | | % Related Substances | | |
|---|---|---|---|---|---|---|---|
| Potency | Sur | B | SA | BA | 0 wks | 2 wks | 4 wks |
| 1 | Poly 80(25) | Cit(1.9) | — | Man(50) | 3.22 | 10.24 | 12.16 |
| 1 | Poly 80(25) | Cit(9.6) | — | Man(50) | 3.36 | 11.74 | 18.63 |
| 1 | Poly 80(25) | Cit(19.2) | — | Man(50) | 3.37 | 17.29 | 22.61 |
| 10 | Poly 80(25) | Cit(9.6) | Suc(50) | — | 3.60 | 5.4 | 6.01 |
| 10 | Poly 80(25) | Cit(9.6) | Tre(50) | — | 3.73 | 4.83 | 6.19 |
| 10 | Poly 80(25) | — | — | Man(50) | 3.98 | 4.85 | 5.45 |
| 10 | Poly 80(25) | Cit(9.6) | Suc(5) | Man(50) | 3.70 | 5.60 | 6.01 |
| 10 | Poly 80(25) | Cit(9.6) | Suc(10) | Man(50) | 3.77 | 5.41 | 5.88 |
| 10 | Poly 80(25) | Tar(1.13) | Fru(10) | Man(50) | 2.49 | — | 2.42 |
| 10 | Poly 80(25) | — | Suc(10) | Man(50) | 4.26 | 4.82 | 4.49 |
| 10 | Poly 80(25) | — | Lac(10) | Man(50) | 4.56 | 4.51 | 4.85 |
| 10 | Poly 80(25) | — | Lac(10) | Man(50) | 4.06 | 5.47 | 5.17 |
| 5 | Poly 80(12.5) | — | Lac(10) | Man(50) | 6.42 | 6.98 | 6.85 |
| 8 | Poly 80 (20) | — | Lac(10) | Man(50) | 5.99 | 6.16 | 5.74 |
| 10 | Poly 80(25) | — | PEG8000(10) | Man(50) | 3.97 | 4.23 | 6.73 |
| 10 | Poly 80(25) | — | PEG6000(10) | Man(50) | 4.13 | 4.47 | 8.11 |

We claim:

1. A stabilized freeze-dried formulation comprising
(i) an echinocandin compound, or a pharmaceutically acceptable salt thereof;
(ii) a pharmaceutically acceptable micelle-forming surfactant with an HLB value of 10-18;
(iii) a bulking agent; and
(iv) a stabilizing agent,
wherein said micelle-forming surfactant is present in said freeze-dried formulation in an amount greater than 5% by weight, and at a weight ratio of echinocandin compound to surfactant from about 1:1.75 to about 1:25;
wherein said micelle-forming surfactant is not a block copolymer of propylene oxide and ethylene oxide;
wherein, upon freeze drying, said freeze-dried formulation is a well-formed cake suitable for reconstitution as a parenteral pharmaceutical formulation suitable for intramuscular, intravenous or subcutaneous administration;
wherein said echinocandin compound is represented by the following structure:,

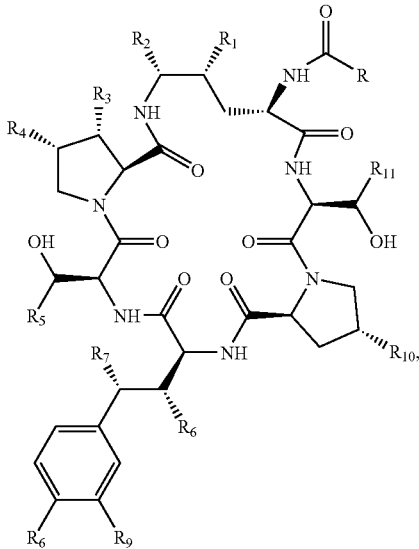

wherein:
R is a group having the structure:

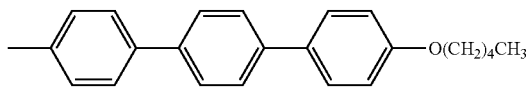

wherein $R_1$, $R_2$, $R_3$, $R_6$, $R_7$, and $R_{10}$ are hydroxy;
$R_4$ is methyl;
$R_5$ and $R_{11}$ are methyl;
$R_8$ is —OH;
$R_9$ is —H; and
pharmaceutically acceptable salts thereof;
wherein said bulking agent is selected from the group consisting of mannitol, glycine, sucrose, trehalose, lactose, dextran, hydroxyethyl starch, ficoll and gelatin; and
wherein said stabilizing agent is a carbohydrate.

2. The formulation of claim 1 wherein said micelle-forming surfactant is a polysorbate, a polyoxyethylene castor oil derivative, a polyoxyethylene stearate, or combinations thereof.

3. The formulation of claim 1 wherein said surfactant is a combination of micelle-forming surfactants with HLB values of 10-18.

4. The formulation of claim 3 wherein said weight ratio of echinocandin to surfactant is from about 1:2 to about 1:3.

5. The formulation of claim 1 further comprising a buffer.

6. The formulation of claim 5 where the buffer is selected from the group consisting of acetates, citrates, tartrates, lactates, succinates and phosphates and amino acids.

7. The formulation of claim 5 where the buffer is an acetate, citrate, or tartrate.

8. The formulation of claim 1 wherein the stabilizing agent is sucrose, fructose, trehalose or combinations thereof.

9. The formulation of claim 1 wherein the bulking agent is mannitol, sucrose, trehalose, lactose or combinations thereof.

10. The formulation of claim 1 wherein the stabilizing agent is fructose, or trehalose and the bulking agent is mannitol, lactose or combinations thereof.

11. The formulation of claim 7 wherein the stabilizing agent is fructose or trehalose and the bulking agent is mannitol, lactose or combinations thereof.

12. The formulation of claim 1 wherein said stabilizing agent is fructose, sucrose or trehalose, said bulking agent is mannitol or lactose, and said micelle forming surfactant is a polysorbate.

13. The formulation of claim 5 wherein said stabilizing agent is fructose, sucrose or trehalose, said bulking agent is mannitol or lactose, said micelle forming surfactant is a polysorbate, and said buffer is an acetate, citrate, or tartrate.

14. The formulation of claim 1 wherein said echinocandin compound is present prior to freeze drying at a concentration from 1 mg/ml to 30 mg/ml.

15. The formulation of claim 1 wherein said echinocandin compound is present prior to freeze drying at a concentration from 8 mg/ml to 12 mg/ml.

16. The formulation of claim 12 wherein said echinocandin compound is present prior to freeze drying at a concentration from 1 mg/ml to 30 mg/ml.

17. The formulation of claim 12 wherein said echinocandin compound is present prior to freeze drying at a concentration from 8 mg/ml to 12 mg/ml.

18. A parenteral formulation comprising the stabilized freeze-dried formulation of claim 1 and an aqueous solvent.

19. The formulation of claim 18 further comprising a buffer.

20. The formulation of claim 19 wherein said buffer is selected from the group consisting of acetates, citrates, tartrates, lactates, succinates, phosphates and amino acids.

21. The formulation of claim 20 where the buffer is an acetate, citrate, or tartrate.

22. A process for making the stabilized freeze-dried formulation according to claim 1 comprising in the following order the steps of:
  (i) dissolving into an aqueous solvent an echinocandin compound or echinocandin/carbohydrate complex containing said echinocandin compound in the presence of a pharmaceutically acceptable micelle-forming surfactant with an HLB value of 10-18 to form a solution, wherein said surfactant is present in an amount greater than 1% weight per volume of solution;
  (ii) sterile filtering said solution; and
  (iii) freeze-drying said solution;
  further comprising the step of adding one or more bulking agents and one or more stabilizing agents before step (ii)
  wherein said micelle-forming surfactant is not a block copolymer of propylene oxide and ethylene oxide;
  wherein said micelle-forming surfactant is present in said freeze-dried formulation in an amount greater than 5% by weight, and at a weight ratio of echinocandin to surfactant from 1:1.75 to 1:25;
  wherein the freeze dried formulation is a well-formed cake suitable for reconstitution as a parenteral pharmaceutical formulation suitable for intramuscular, intravenous or subcutaneous administration;
  wherein said bulking agent is selected from the group consisting of mannitol, glycine, sucrose, trehalose, lactose, dextran, hydroxyethyl starch, ficoll and gelatin;
  wherein said stabilizing agent is a carbohydrate; and
  wherein said echinocandin compound is represented by the following structure:

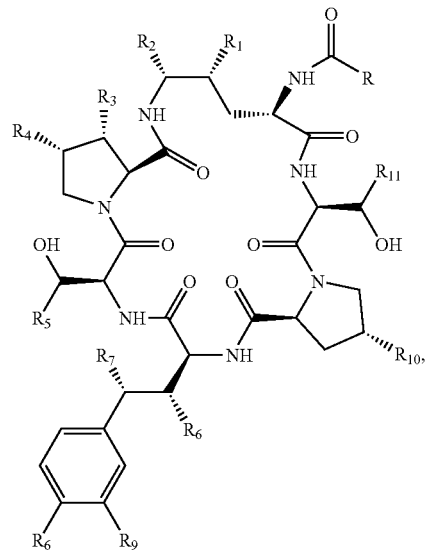

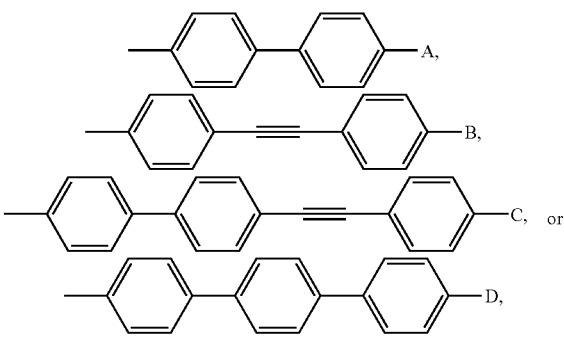

wherein

R is a group having the structure:

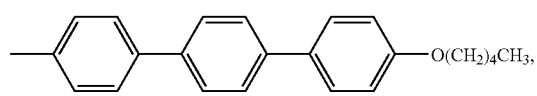

wherein $R_1$, $R_2$, $R_3$, $R_6$, $R_7$, and $R_{10}$ are hydroxy;

$R_4$ is methyl;

$R_5$ and $R_{11}$ are methyl;

$R_8$ is —OH;

$R_9$ is —H; and pharmaceutically acceptable salts thereof.

23. The process of claim 22 further comprising the step of adding one or more buffers, tonicity agents, combinations thereof before step (ii).

24. The process of claim 22 wherein said micelle-forming surfactant is a polysorbate, polyoxyethylene castor oil derivative, polyoxyethylene stearate, or combinations thereof.

25. The process of claim 22, wherein said micelle-forming surfactant is a combination of micelle-forming surfactants with HLB values of 10-18.

26. A process for preparing a stabilized freeze-dried formulation according to claim 1 comprising the steps of
  (i) buffering a non-toxic aqueous solvent to a pH between 4.0 and 5.5 to form a buffered solution;

(ii) adding to said buffered solution a pharmaceutically acceptable, micelle-forming surfactant with an HLB value of 10-18;
(iii) cooling the solution from step (ii) to a temperature between 5° and 15° C. to form a cooled solution;
(iv) adding a slurry comprising an echinocandin compound or echinocandin/carbohydrate complex containing said echinocandin compound and a second non-toxic aqueous solvent to said cooled solution;
(v) sterile filtering said solution from step (iv); and
(vi) freeze-drying said solution from step (v);
further comprising the step of adding one or more bulking agents and one or more stabilizing agents before step (v);
wherein said micelle-forming surfactant is not a block copolymer of propylene oxide and ethylene oxide;
wherein said micelle-forming surfactant is present in said freeze-dried formulation in an amount greater than 5% by weight, and at a weight ratio of echinocandin to surfactant from 1:1.75 to 1:25; and
wherein the freeze dried formulation is a well-formed cake suitable for reconstitution as a parenteral pharmaceutical formulation suitable for intramuscular, intravenous or subcutaneous administration;
wherein said bulking agent is selected from the group consisting of mannitol, glycine, sucrose, trehalose, lactose, dextran, hydroxyethyl starch, ficoll and gelatin:
wherein said stabilizing agent is a carbohydrate; and
wherein said echinocandin compound is represented by the following structure:

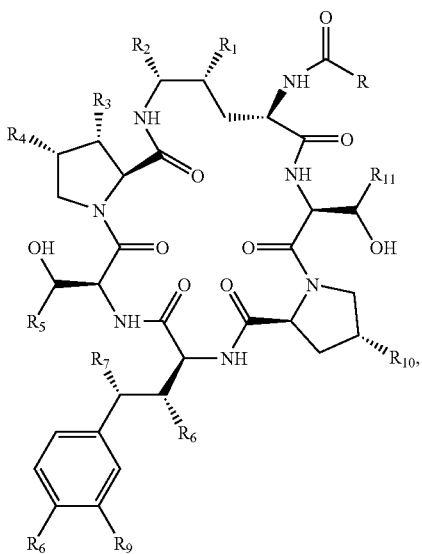

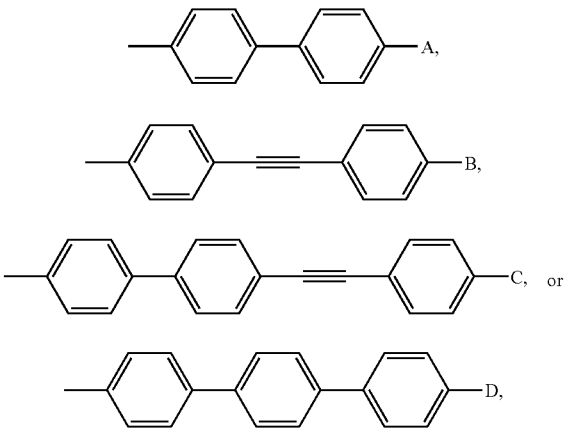

wherein
R is a group having the structure:

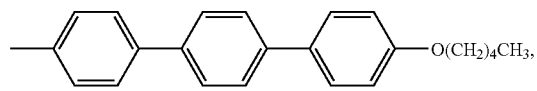

wherein $R_1$, $R_2$, $R_3$, $R_6$, $R_7$, and $R_{10}$ are hydroxy;
$R_4$ is methyl;
$R_5$ and $R_{11}$ are methyl;
$R_8$ is —OH;
$R_9$ is —H; and
pharmaceutically accentable salts thereof;
wherein said bulking agent is selected from the group consisting of mannitol, glycine, sucrose, trehalose, lactose, dextran, hydroxyethyl starch, ficoll and gelatin; and
pharmaceutically acceptable salts thereof.

27. The process of claim 26 wherein said temperature in step (iii) is from about 7° C. to about 10° C.

28. A method of treating a fungal infection in a mammal in need thereof comprising the step of administering to said mammal a parenteral formulation of claim 18.

29. A method of treating a fungal infection in a mammal in need thereof comprising the step of administering to said mammal a parenteral formulation of claim 19.

* * * * *

UNITED STATES PATENT AND TRADEMARK OFFICE
CERTIFICATE OF CORRECTION

| | | |
|---|---|---|
| PATENT NO. | : 7,709,444 B2 | Page 1 of 1 |
| APPLICATION NO. | : 11/103798 | |
| DATED | : May 4, 2010 | |
| INVENTOR(S) | : Nathaniel Milton et al. | |

It is certified that error appears in the above-identified patent and that said Letters Patent is hereby corrected as shown below:

Title Page, Item (73) Assignee-- Delete Assignee "Pfizer, Inc., New York, NY (US)"

Replace with: -- Eli Lilly and Company, Indianapolis, IN (US) --

Signed and Sealed this

Fourteenth Day of September, 2010

David J. Kappos
*Director of the United States Patent and Trademark Office*